United States Patent

Ramamurthy et al.

[11] Patent Number: 5,846,202
[45] Date of Patent: Dec. 8, 1998

[54] ULTRASOUND METHOD AND SYSTEM FOR IMAGING

[75] Inventors: Bhaskar Ramamurthy, San Jose; J. Michael Green, Pleasanton, both of Calif.

[73] Assignee: Acuson Corporation, Mountain View, Calif.

[21] Appl. No.: 990,311

[22] Filed: Dec. 15, 1997

Related U.S. Application Data

[63] Continuation-in-part of Ser. No. 692,865, Jul. 30, 1996, Pat. No. 5,709,210.

[51] Int. Cl.⁶ .................................................. A61B 8/00
[52] U.S. Cl. ............................................................ 600/450
[58] Field of Search ..................... 600/441, 437, 600/448, 450, 453, 454, 455, 456, 458

[56] References Cited

U.S. PATENT DOCUMENTS

| | | |
|---|---|---|
| 3,640,271 | 2/1972 | Horton . |
| 4,712,037 | 12/1987 | Verbeek et al. . |
| 5,099,847 | 3/1992 | Powers et al. . |
| 5,111,823 | 5/1992 | Cohen . |
| 5,115,809 | 5/1992 | Saitoh et al. . |
| 5,135,000 | 8/1992 | Akselrod et al. . |
| 5,148,810 | 9/1992 | Maslak et al. . |
| 5,188,112 | 2/1993 | Sturgill et al. . |
| 5,195,520 | 3/1993 | Schlief et al. . |
| 5,197,477 | 3/1993 | Peterson et al. . |
| 5,211,169 | 5/1993 | Freeland . |
| 5,233,994 | 8/1993 | Shmulewitz . |
| 5,255,683 | 10/1993 | Monaghan . |
| 5,285,788 | 2/1994 | Arenson et al. . |
| 5,287,753 | 2/1994 | Routh et al. . |
| 5,313,948 | 5/1994 | Murashita et al. . |
| 5,358,466 | 10/1994 | Aida et al. . |
| 5,386,830 | 2/1995 | Powers et al. . |
| 5,396,285 | 3/1995 | Hedberg et al. . |
| 5,409,688 | 4/1995 | Quay . |
| 5,410,205 | 4/1995 | Gururaja . |
| 5,410,516 | 4/1995 | Uhlendorf et al. . |
| 5,417,213 | 5/1995 | Prince . |
| 5,417,214 | 5/1995 | Roberts et al. . |
| 5,425,366 | 6/1995 | Reinhardt et al. . |
| 5,431,161 | 7/1995 | Ryals et al. . |
| 5,433,207 | 7/1995 | Pretlow, III . |
| 5,438,554 | 8/1995 | Seyed-Bolorforosh et al. . |
| 5,443,071 | 8/1995 | Banjanin et al. . |
| 5,456,255 | 10/1995 | Abe et al. . |
| 5,456,257 | 10/1995 | Johnson et al. . |
| 5,469,849 | 11/1995 | Sasaki et al. . |
| 5,471,990 | 12/1995 | Thirsk . |
| 5,479,926 | 1/1996 | Ustuner et al. . |
| 5,482,046 | 1/1996 | Deitrich . |
| 5,523,058 | 6/1996 | Umemura et al. ............. 600/437 |
| 5,526,816 | 6/1996 | Arditi . |
| 5,533,510 | 7/1996 | Koch, III et al. . |
| 5,540,909 | 7/1996 | Schutt . |
| 5,558,092 | 9/1996 | Unger et al. . |
| 5,560,364 | 10/1996 | Porter . |

(List continued on next page.)

FOREIGN PATENT DOCUMENTS

| | | |
|---|---|---|
| 0 357 164 | of 0000 | European Pat. Off. . |
| 0 770 352 A1 | 5/1997 | European Pat. Off. . |

OTHER PUBLICATIONS

T.G. Leighton, "Transient excitation of insonated bubbles." Research Notes.

(List continued on next page.)

Primary Examiner—George Manuel
Attorney, Agent, or Firm—Brinks Hofer Gilson & Lione

[57] ABSTRACT

Color Doppler data is acquired only over a portion of the cardiac cycle, such as during diastole in order to increase the sensitivity of detection. Ultrasound system parameters such as clutter filter coefficience, temporal and spatial filter coefficients and demodulation frequencies may be altered only for a portion of the cardiac cycle to increase detection sensitivity, to improve myocardial border estimation and to avoid the loss of color Doppler image at end-diastole.

24 Claims, 9 Drawing Sheets

U.S. PATENT DOCUMENTS

| | | |
|---|---|---|
| 5,577,505 | 11/1996 | Brock-Fisher et al. . |
| 5,579,768 | 12/1996 | Klesenski . |
| 5,579,770 | 12/1996 | Finger . |
| 5,588,435 | 12/1996 | Weng et al. . |
| 5,601,085 | 2/1997 | Ostensen et al. . |
| 5,601,086 | 2/1997 | Pretlow, III et al. . |
| 5,608,690 | 3/1997 | Hossack et al. . |
| 5,617,862 | 4/1997 | Cole et al. . |
| 5,628,322 | 5/1997 | Mine . |
| 5,632,277 | 5/1997 | Chapman et al. . |

OTHER PUBLICATIONS

Eric J. Chen, et al., "Young's Modulus Measurements of Soft Tissues with Application to Elasticity Imaging." IEEE Transactions on Ultrasonics, Ferroelectrics, and Frequency Control, vol. 43, No. 1, Jan .1996.

Pi Hsien Chang, et al., "Second Harmonic Imaging and Harmonic Doppler Measurements with Albunex." IEEE Transactions on Ultrasonics, Ferroelectrics, and Frequency Control, vol. 42, No. 6, Nov. 1996.

Marc Gensane, "Bubble population measurements with a parametric array." 1994 Acoustical Society of America, 95(6) Jun.

Ken Ishihara et al., "New Approach to Noninvasive Manometry Based on Pressure Dependent Resonant Shift of Elastic Microcapsules in Ultrasonic Frequency Characteristics." Japanese J. of Applied Physics, vol. 2 (1988).

Shmuel Gottlieb, M.D. et al., "Effect of Pressure on Echocardiographic Videodensity from Sonicated Albumin: An In Vitro Model." J. Ultrasound Med. 14 (1995).

J. W. Norris, "The non–linear oscillation of a radially symmetric bubble in a time periodic pressure field." Dynamics and Stability of Systems, vol. 9, No. 1 (1994).

Michael S. Longuet–Higgins, Resonance in nonlinear bubble oscillations. J. Fluid Mech. (1991) vol. 224.

Chiang C. Mei, et al., "Parametric resonance of a spherical bubble." J. Fluid Mech. (1991) vol. 229.

V.L. Newhouse, et al., "Bubble size measurements using the nonlinear mixing of two frequencies." J. Acoust. Soc. Am. 75(5), May 1984.

Janet B. Jones–Oliveira, et al., "Transient fluid—solid interaction of submerged spherial shells revisited: Proliferation of frequencies and acoustic radiation effects." Acoustical Society of America, 96(2) Pt. 1, Aug. 1994.

Chandra M. Sehgal, PhD., et al., "Sonographic Enhancement of Renal Cortex by Contrast Media." J. Ultrasound Med, 14 (1995).

"Abstract Session IV Contrast and Ischemia." and Abstract Session X TEE and Source of Embolus Journal of the American Society of Echocardiography, vol. 8, No. 3, May 1995.

Chandra M. Sehgal, PhD, et al., "Influence of Postprocessing Curves on Contrast—Echographic Imaging: Preliminary Studies." J. Ultrasound Med, 14 (1995).

Deborah J. Rubens, M.D., et al., "Sonoelasticity Imaging of Prostate Cancer: In Vitro Results." Radiology, vol. 995, No. 2, 1995.

Kotaro Sato, et al., "Numerical analysis of a gas bubble near a rigid boundary in an oscillatory pressure field." J. Acoustical Society of America, 95(5), May 1994.

L.W. Anson et al., "Ultrasonic scattering from spherical shells including viscous and thermal effects." J. Acoustical Society of America, 93 (4), Apr. 1993.

B. Schrope, et al., "Simulated Capillary Blood Flow Measurement Using A Nonlinear Ultrasonic Contrast Agent," Ultrasonic Imaging 14 (1992).

Fred Lee, Jr., M.D., et al., "Sonoelasticity Imaging: Results In In Vitro Tissue Specimens." Radiology, vol. 181, No. 1, 1991.

Kevin J. Parker, PhD, et al., "Sonoelasticity of Organs: Shear Waves Ring a Bell." J. Ultrasound Med., 11 (1992).

William Armstrong, M.D., et al., "American Society of Echocardiography Position Paper on Contrast Echocardiography." draft 1—Jun. 6, 1994.

K.J. Parker, et al., "Tissue Response to Mechanical Vibrations for 'Sonoelasticity Imaging'." Ultrasound in Med. & Biol., vol. 16, No. 3, (1990).

Robert M. Lerner, et al., "'Sonoleasticity' Images Derived from Ultrasound Signals in Mechanically Vibrated Tissues."Ultrasound in Med. & Biol., vol. 16, No. 3, (1990).

J. Ophir, et al., "Elastography: A Quantitative Method for Imaging the Elasticity of Biological Tissues." Ultrasonics Imaging 13 (1991).

J.A. Hossack et al., "Improving transducer performance using multiple active layers." SPIE vol. 1733 (1992).

Volkmar Uhlendorf, et al., "Nonlinear Acoustical Response of Coated Microbubbles in Diagnostic Ultrasound." 1994 Ultrasonics Symposium.

John A. Hossack, et al., "Improving the Characteristics of a Transducer Using Multiple Piezoelectric Layers." IEEE Transactions on Ultrasonics, Ferroelectrics, and Frequency Control, vol. 40, No. 2, Mar. 1993.

H. Edward Karrer, et al., "A Phased Array Acoustic Imaging System for Medical Use." 1980 Ultrasonics Symposium.

"HP Ultrasound Technologies—Viability." About HP Ultrasound Imaging, WWW document, 1997.

Ted Christopher, "Finite Amplitude Distortion–Based Inhomogeneous Pulse Echo Ultrasonic Imaging." IEEE Transactions on Ultrasonics, Ferroelectrics, and Frequency Control, vol. 44, No. 1, Jan. 1997.

"Supplement to Journal of the American College of Cardiology" American College of Cardiology, $45^{th}$ Annual Scientific Session, Mar. 24–27, 1996 pp. 21A, 63A, 239–240A.

Yang–Sub Lee, et al., "Time–domain modeling of pulsed finite–amplitude sound beams." 1995 Acoustical Society of America, 97 (2), Feb. 1995.

Michalakis A. Averkiou, et al., "Self–demonstration of amplitude–and frequency–modulated pulses in a thermoviscous fluid." J. Acoustical Society of America, 94 (5), Nov. 1993.

New Quantitation of Approaches to Contrast Enhancement, Armstrong et al., University of Michigan, Ann Arbor, Michigan, Jun. 1996.

Innovative Imaging Modalities: Harmonic Imaging, Power Doppler Imaging, and Triggered Mode Imaging: Concepts and Instrumentation, Powers et al., Advanced Technology Laboratories, Inc., University of Toronto, Jun. 1996.

Harmonic Imaging and Single Frame "Triggered Mode" Data Acquisition Enhance Delineation of Myocardial Perfusion Defects by Volume–Rendered 3–Dimensional Echocardiography, Cao et al., Tufts–New England Medical Center, Boston, Massachusetts, Jun. 1996.

An ECG–Gated Color Doppler Imaging System for Determination of Coronary Bypass Graft Patency, Klepper et al., Institute of Applied Physiology and Medicine, pp. 203–212, Apx. 1985.

ULTRASOUND METHOD AND SYSTEM FOR IMAGING

RELATED APPLICATION

The present application is a continuation-in-part of the U.S. application for a ULTRASOUND SYSTEM FOR IMAGING, Ser. No. 08/692,865, filed on Jul. 30, 1996, now U.S. Pat. No. 5,709,210 the disclosure of which is hereby incorporated by reference.

BACKGROUND OF THE INVENTION

This invention relates in general to ultrasound imaging, and in particular to an ultrasound system for imaging tissue and/or blood flow where the imaging is performed in response to a cardiac cycle, such as that of a human or animal.

In clinical analysis, it is important to determine myocardial perfusion and color Doppler velocity or energy mapping of the ventricles and preservation of intra-cardiac blood pool images. Information on myocardial perfusion would allow the clinician to more accurately diagnose coronary and heart function. Mapping of the ventricles permits improved myocardial border estimations and the preservation of intra-cardiac blood pool images allow the clinician to measure the blood pool.

Previous methods used to determine myocardial perfusion include direct imaging methods such as doubutamine magnetic resonance imaging, thallium-201 imaging, technetium-99 imaging and myocardial contrast echocardiography. Indirect methods look at the velocity or relative motion of the heart wall and include stress echocardiography and Doppler determined wall velocities.

Ventricular angiography is used to determine ventricular borders, ejection fractions and cardiac output.

CD (color Doppler) capture is also currently available for ultrasound imaging systems. Cumulative color Doppler signals over multiple beats are overlaid on a real-time 2-D reference image. As currently implemented, the CD capture function displays the highest mean velocities detected at each point in the image during a selected time interval. Interval options are one, two, four, and eight seconds. Once activated, the display of the highest mean velocity remains on the screen. If a subsequent mean velocity at the same spatial location is of a greater magnitude, it replaces the initial sample. Since color sample points are measures of mean velocity, the display is created by accumulating the maximum (or peak) mean velocities. B-mode is active continuously during the selected intervals and is frozen when the selected interval end-point is reached.

The acquisition of data is unaffected by invoking the CD capture feature, except that when the end of interval is reached the imaging of the acquisition stops. The interval sometimes can also be of indefinite length; in such event the user still specifies a time interval and the CD frames are accumulated for the selected time interval and then a fresh cycle of accumulation starts. This process continues until the user instructs the system to stop. Here too, the acquisition is not controlled.

EKG (electrocardiogram) trigger is currently available on most cardiology ultrasound imaging systems. In its current implementation, one or two separate trigger points are selected along an EKG waveform. In its most usual implementation, the EKG signal triggers the acquisition of one frame of ultrasound data. The data is displayed on the screen till the next trigger comes along and the process is repeated. The acquisition includes transmission, reception and scan conversion of ultrasound data. More than one trigger point is also allowed in some machines. At each trigger point, one frame is acquired. The triggered operation is continued till the feature is de-selected.

There are many disadvantages with the above methods. Current myocardial contrast echocardiography is insensitive and patients experience frequent side effects from the contrast agents. Thallium and technetium scanning involve expensive radioisotopes with short shelf lives. Doubutamine MRI is currently undergoing clinical trials and many patients poorly tolerate MRI examination. Indirect methods fail to differentiate between viable myocardium from stunned or hibernating myocardium and are insensitive and difficult to apply.

Techniques used to determine the cavity area, cross-sectional size or ventricular function, as in the case of ventricular angiography, are expensive and time consuming. Ultrasonic methods to similarly measure and evaluate the cardiac chambers are prone to numerous inaccuracies.

Even though CD (color Doppler) capture is useful for cardiac applications, further improvements can be made. For cardiac applications, it is desirable to be able to select from a range of desired B-mode and color Doppler behaviors and interactions. In CD capture as currently implemented, B-mode and color Doppler image acquisition is halted at the end of a pre-selected interval. This does not allow for serial comparisons of Doppler detected changes over time. Also, CD capture is not triggered by any signals originating from the body. The acquisition and display of CD frames is not synchronized with any events in the body. Currently, the user decides when to activate CD capture, based on his or her understanding of the events that are visualized with B-mode displays.

It is therefore desirable to provide an improved ultrasound imaging system with improved capability for detecting myocardial perfusion, for mapping of the ventricles and for preservation of intra-cardiac blood pool images as well as other imaging functions.

SUMMARY OF THE INVENTION

An ultrasound imaging system with an improved capability for detecting myocardial perfusion, for mapping of the ventricles and for preservation of intra-cardiac blood pool images is provided.

A first aspect of the invention is directed to a method and apparatus for ultrasonic imaging. Waveform information is provided on an input. Begin and end triggers are generated in response to the waveform information. In response to the begin trigger, a plurality of frames of imaging data is acquired. Each of the plurality of frames is associated with a harmonic frequency band. The acquisition of step (b) is ended in response to the end trigger.

In a second aspect of the invention, the waveform information includes cardiac cycle information. The begin and end signals are associated with first and second points, respectively, in a cardiac cycle. At least one frame of B-mode information is acquired during the cardiac cycle. In response to the begin and end signals, a plurality of frames of imaging information associated with harmonic frequencies is acquired. The imaging information is selected from the group of: B-mode information and color Doppler information.

In a third aspect of the invention, the begin and end signals are associated with first and second points, respectively, in a cardiac cycle. At least a first frame of B-mode information is acquired during the cardiac cycle. A plurality of frames of imaging information in addition to the at least a first frame of B-mode information is acquired during the cardiac cycle. The imaging information is associated with harmonic frequencies and selected from the group of: B-mode information and color Doppler information. In response to the begin signal, at least one parameter associated with acquiring the plurality of frames of imaging information is altered. In response to the end signal, the at least one parameter is again altered.

BRIEF DESCRIPTION OF THE DRAWINGS

For simplicity in description, identical components in this application are identified by the same numerals.

DETAILED DESCRIPTION OF THE PREFERRED EMBODIMENT

Figure 1:
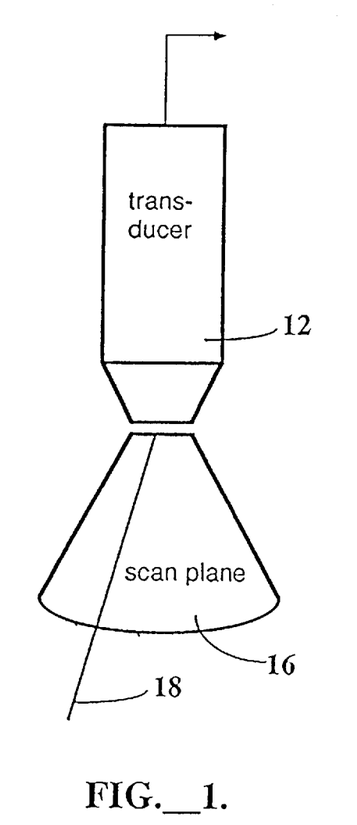
FIG. 1 is a block diagram of a transducer of an ultrasound imaging system for imaging tissue and blood flow to illustrate the invention.
Figure 2A:
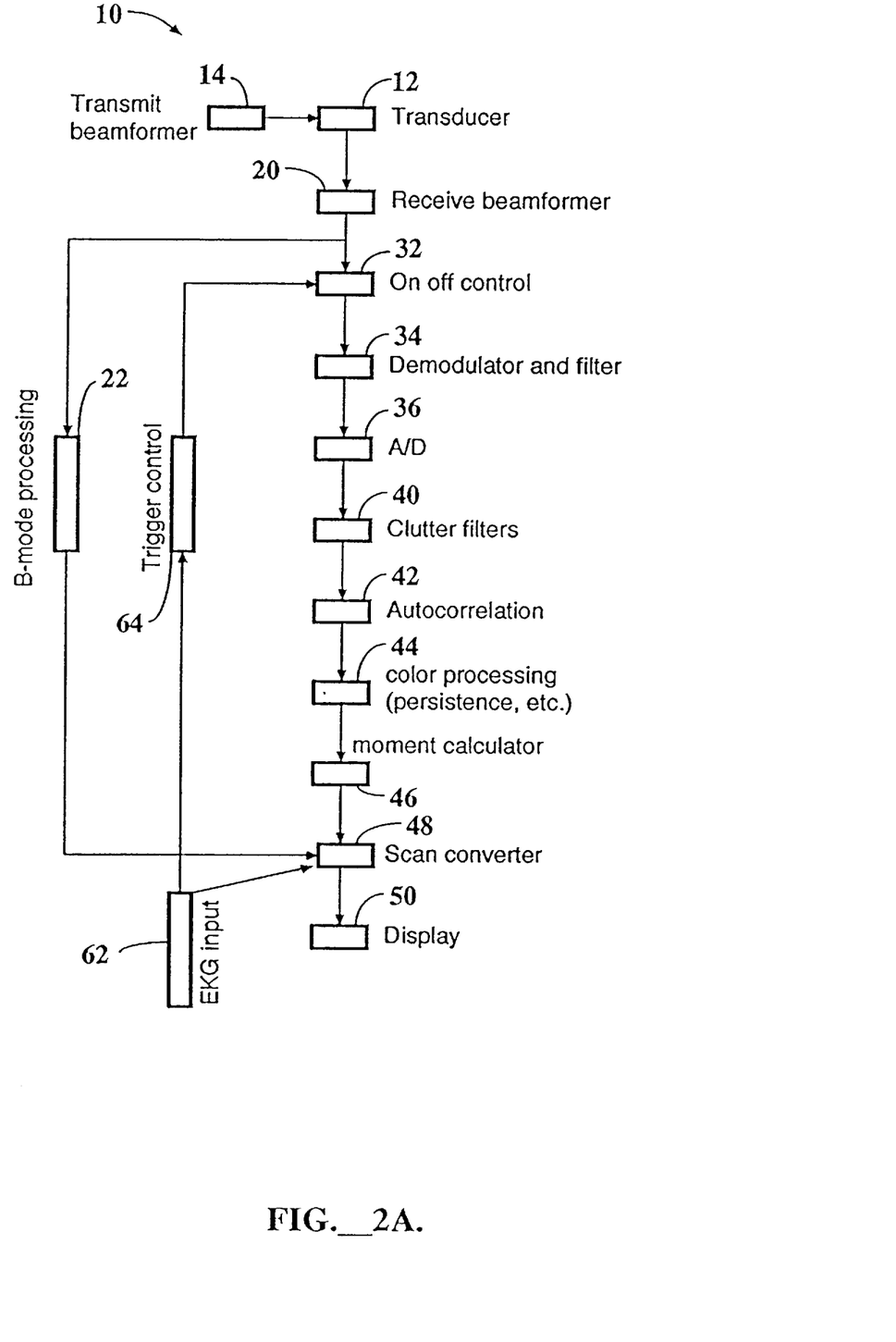
FIG. 2A is a block diagram of an ultrasound imaging system for illustrating a first embodiment of the invention.

FIG. 1 is a block diagram of a transducer of an ultrasound imaging system for imaging a body to illustrate the invention. FIG. 2A is a block diagram of an ultrasound imaging system to illustrate a first embodiment of the invention. In reference to FIGS. 1 and 2A, the transducer 12 is excited by a transmit beamformer 14 to propagate ultrasound energy bursts into a body on a scan plane 16. In a manner known to those skilled in the art, the transmit beamformer 14 and receive beamformer 20 are used to electronically steer scan line 18 to cover the entire scan plane 16 to obtain a frame of imaging data for the tissue and/or blood flow in the scan plane. Thus, while the transducer 12 remains stationary relative to scan plane 16, the transmit and receive beamformers 14, 20 are operated to electronically steer scan line 18 across scan plane 16 for imaging tissue and/or blood flow. Techniques for steering a scan line are described, for example, in U.S. Pat. No. 5,148,810.

The B-mode gray scale data acquired comprises a B-mode data frame, and the Doppler signal data so acquired comprises a frame of Doppler data. If displayed in color, the Doppler frame is referred to herein as a frame of color Doppler data. The Doppler data displayed may include energy, mean velocity, variance of velocity estimate or a parameter which is a function of a combination of one or more of the three quantities in various different display modes. A combined mean velocity and energy mode is described, for example, in pending U.S. patent application Ser. No. 08/367,064, filed Dec. 30, 1994, entitled "Imaging Modality Showing Energy And Velocity," which is incorporated herein by reference. The receive beamformer 20 supplies the B-mode data to a B-mode data path which includes a B-mode processing unit 22 and the Doppler data to a color Doppler data path which includes an on/off control switch 32, modulator and filter 34 for converting the signal to baseband and to be digitized by A/D converter 36, as well as other components described below.

Using the receive beamformer 20, the imaging system is preferably configurable to acquire signals associated with a fundamental frequency band or with a harmonic frequency band. Harmonic frequencies are frequencies associated with non-linear propagation (tissue) or non-linear scattering (tissue or contrast agents) of transmit signals. As used herein, harmonic includes subharmonics as well as second, third, fourth, and other harmonics. Fundamental frequencies are frequencies corresponding to linear propagation and linear scattering of transmit signals. Thus, the imaging system generates images based on fundamental or harmonic band information. The receive bandwidth may include harmonic band and fundamental band information.

Harmonic band based imaging can be used for both tissue and contrast agent harmonic imaging. In contrast agent harmonic imaging, any one of a number of well known nonlinear ultrasound contrast agents is added to the target or subject in order to enhance the signal from fluid (blood). These contrast agents radiate ultrasonic energy at a harmonic of the fundamental frequency insonifying energy. Other contrast agents may be used to radiate ultrasonic energy at fundamental frequencies.

Medical ultrasound imaging is typically conducted in a discrete imaging session for a given subject at a given time. For example, an imaging session can be limited to an ultrasound patient examination of a given tissue of interest over a period of ¼ to 1 hour, though other durations are possible. In tissue harmonic imaging, no additional non-linear contrast agent is added to the target any time during the imaging session, and the native nonlinear characteristics of the tissue are relied on to create the harmonic band based ultrasonic image. Since the harmonic imaging techniques described above can be used for both tissue and contrast agent harmonic imaging, it should be understood that the introduction of an added nonlinear contrast agent into the tissue being imaged is not implied in any of the following claims unless such added non-linear contrast agent is expressly recited.

A user interface provides a means for selecting between harmonic, fundamental and combination fundamental and harmonic imaging. For example, the user provides input corresponding to a transmit frequency and a receive frequency, such as by selecting a harmonic transmit value. Programming may be used instead of user selection. The selected frequencies associated with each image are within the frequency range of the transducer 12.

Based on the user input, the transmit beamformer 14 is configured to transmit a plurality of excitation signals as discussed above. Each excitation signal has an associated center frequency and a bandwidth. The center frequency and bandwidth are selected as optimum values for the particular imaging situation. Preferably, the center frequency of the excitation signals is within the 1 to 15 MHz range, such as 1.75 MHz for harmonic imaging, and accounts for the frequency response of the transducer 12. Except for CW spectral Doppler, the excitation signals preferably have non-zero bandwidth.

As discussed above, one or more of the elements in the transducer 12 are excited by an excitation signal to produce ultrasonic waves. The ultrasonic waves have a center frequency, such as 1.75 MHz, and a bandwidth determined by the excitation signals and the spectrum of the transducer 12.

As discussed above, the focused ultrasonic waves propagate through a body and reflect or scatter off various structures, such as blood cells and tissue, both linearly and non-linearly. Some of the reflected waves return as echo signals to the transducer 12. The echo signals excite the elements of the transducer 12. The elements generate voltage signals corresponding to the echo signals. These voltage signals are provided to the receive beamformer 20. The transmit and receive beamformers 14 and 20 may comprise a combined receive and transmit beamformer. As known in the art, the receive beamformer 20 delays, apodizes, and sums the voltage signals. An ongoing stream of summed signals represents the ultrasound beam or line received from the body.

The receive beamformer 20 or other components in the B-mode receive path are configured to form images with the desired frequency band. Thus, images can be formed with the fundamental frequencies, the harmonic frequencies or a combination of frequency bands. Preferably, a configurable filter in the receive path is configurable to pass the signals with the desired frequency content.

Similar filtering can be applied to the received signals to form Doppler images with the desired frequency content. A filter is placed in the signal path in the receive beamformer 20 to enable the color Doppler path and the B-mode path to form images with the desired frequency band. Alternatively, the B-mode path and the Doppler path can each have independent filters to accomplish the same operation.

Preferably, the Doppler data is obtained using fundamental frequency band information, and the B-mode data is obtained using either fundamental or harmonic frequency band information. The Doppler data may be based on harmonic frequency information. The Doppler data and B-mode data is then further processed as discussed below.

For blood flow information from the Doppler return to be detected, Doppler components that arise from stationary or slowly moving structures such as vessel walls are removed or reduced by the clutter filters 40 from the digitized output of converter 36. The filtered signals are then sent to a processor 42 which calculates the zero and first order autocorrelation lag values. These values are typically then filtered by temporal filters in color processing unit 44, assuming that autocorrelation values for multiple acoustic frames are available at this point. Then the mean velocity, variance and energy are calculated in the moment calculator 46 using the filtered autocorrelation values for each acoustic frame. This information and the B-mode information from processing unit 22 is then scan-converted by scan converter 48 to be displayed as B-mode and color Doppler information. The scan-converted color Doppler information and the B-mode information is then supplied to monitor 50 for display.

Figure 2B:
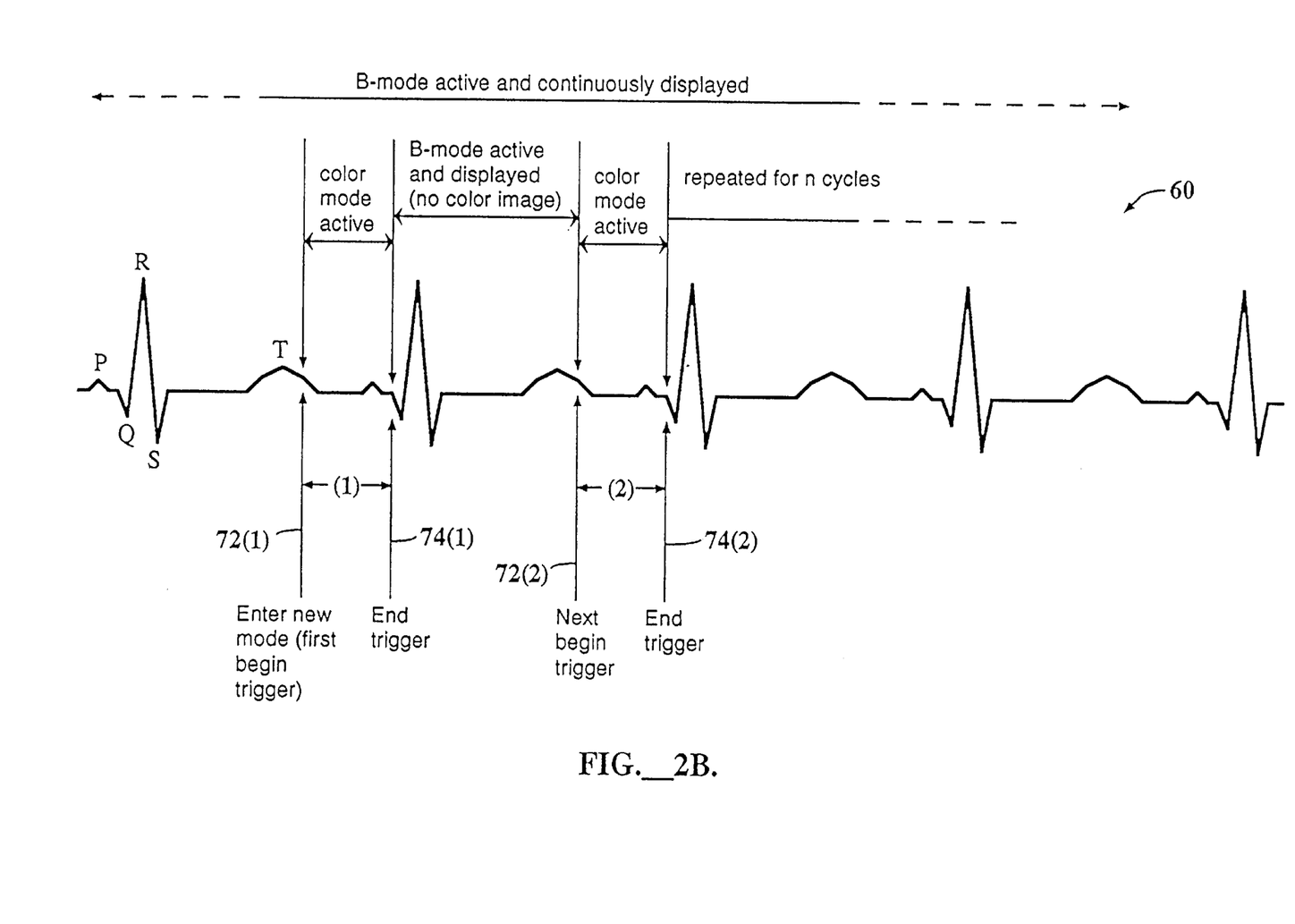
FIG. 2B is a graphical illustration of the EKG waveform to illustrate the operation of the system of FIG. 2A.

FIG. 2B is a graphical illustration of an EKG waveform 60 to illustrate the operation of the system 10 of FIG. 2A. As shown in FIG. 2B, the EKG waveform 60 includes multiple cardiac cycles, where each cycle includes a R-wave, S-wave, T-wave, P-wave and a Q-wave. The R-wave in the cardiac cycle is the point in time when the heart contracts. Thus, during this point of the cardiac cycle, motion of the heart wall is at a peak value and will generate high amplitude Doppler signals. The portion of the cardiac cycle between the T-wave and the R-wave of the next cardiac cycle is a period known as diastole. During this time period, the heart vessel walls are essentially at rest.

The inventors realized that, by performing color Doppler data acquisition only during diastole (when coronary artery flow is greatest and heart wall motion is at a minimum) and not during the remaining portion of the cardiac cycle, so that the Doppler return during diastole is not mixed with the Doppler information from heart wall motion, it is possible to improve myocardial perfusion detection sensitivity.

In reference to FIG. 2A, an EKG input is supplied from an EKG input unit 62. The EKG waveform from unit 62 is supplied to trigger control 64. Through a suitable user interface, a user can select the portion of the cardiac cycle in reference to the EKG waveform from unit 62 and provide trigger signals to be supplied to on/off control switch 32. Such user interface is known to those skilled in the art and will not be described in detail here.

Thus, in reference to FIGS. 2A and 2B, the user may select the time period (1) between times 72(1) and 74(1) in FIG. 2B to be the time period during which color Doppler data is to be acquired and displayed. This and other similar time periods is referred to herein as a data collection cycle. The acquisition and display of color Doppler data in this manner can occur at any time during an ultrasound imaging session, irrespective of whether or not color Doppler data acquisition has been initiated. In the preferred embodiment, a color Doppler mode is initiated in response to a begin signal. For this purpose, preferably a begin trigger is generated by control unit 64 and provided to switch 32 at time 72(1) to begin the color Doppler data acquisition. At the end 74(1) of the data collection cycle (1), an end trigger is provided by control 64 to switch 32 to switch off the color Doppler data path. In this manner, the color Doppler data is acquired during data collection cycle (1) when heart wall motion is at a minimum, where such Doppler data can be displayed distinct from Doppler data from tissue and/or blood flow at instances in other time periods. The above described process can be repeated for additional data collection cycles (2) through N to show continuous images over several cardiac cycles, N being a positive integer. In the preferred embodiment, the on/off control unit 32 may be implemented by a software function for the beamformer, so that the trigger signal from control 64 controls the beamformers 14, 20.

A secondary application of the invention is for color Doppler velocity and energy mapping of the ventricles and preservation of intra-cardiac blood pool images at end-diastole. During the period known as left ventricular diastole, the Doppler velocity falls to zero or close to zero so that it is difficult to detect. This lack of velocity display at diastole is distracting and results in a poorly defined blood pool. However, by application of the new imaging technique outlined above, the ventricular diastole period frame average color Doppler data can be selected and the information content can be temporally persisted. This results in improved myocardial border estimations. This also prevents color from disappearing in the display which is distracting to the clinician. Such change in system parameters is described in more detail below in reference to FIGS. 3A, 3B.

As noted above, the above described data acquisition can be performed during the data collection cycles (1) through (N) over N cardiac cycles. B-mode data acquisition and display is active and continuous to provide B-mode information in a manner unaffected by the begin and end triggers. As also noted above, the color Doppler information disclosed may include mean velocity, energy, variance or a parameter which is a function of any one or a combination of mean velocity, energy and variance. From FIG. 2B it is noted that no color image is displayed except during the data collection cycles.

The value of N may be set from input by a user or preset in the ultrasound system. As used herein, when the B-mode is indicated to be "active and continuous," this means that B-mode data is continuously acquired and displayed as soon as acquired and processed by unit 22 and converter 48; in other words, the B-mode data is displayed in real time. When color Doppler data is displayed as soon as acquired and processed, the color Doppler data is said to be displayed in real time.

The B-mode and/or the color Doppler data displayed is associated with fundamental or harmonic frequency bands. For example, the B-mode data is associated with a fundamental frequency band. The color Doppler data, such as obtained during data collection cycles (1) through (N), is associated with a harmonic, such as the second harmonic, frequency band. Other combinations are possible, such as using B-mode data associated with a harmonic frequency band and color Doppler data associated with a fundamental or harmonic frequency band.

Another combination is the acquisition of fundamental or harmonic band B-mode information throughout the cardiac cycle and of harmonic or fundamental band, respectively, B-mode information during the data collection cycles. By providing appropriate system components, B-mode data instead of color Doppler data is acquired during the data collection cycle. Appropriate system components may include a duplicative B-mode data path or a controller for interleaving harmonic and fundamental based B-mode data acquisitions. Likewise, fundamental or harmonic band color Doppler data may be acquired throughout the cardiac cycle and harmonic or fundamental band, respectively, color Doppler data may be acquired during the data collection cycles.

Contrast agents may also be added to the subject being imaged. Either fundamental or harmonic based information is used to image the subject and the contrast agents. Preferably, the power associated with the acoustic waveforms, such as the waveforms associated with B-mode and color Doppler imaging, is reduced to avoid destruction of the contrast agents, such as substantially no destruction of contrast agents. For example, the system 10 of FIG. 2A transmits waveforms that are 18–20 dB below the system's 10 maximum power. The reduction in power may vary depending on various factors, including the amount of attenuation of the waveform, the system 10 maximum power and the type of contrast agent.

Alternatively, the power may not be reduced. In one embodiment, the waveforms associated with acquiring data during a data collection cycle is substantially at full power. A reduced power waveform is used for imaging throughout plurality of cardiac cycles. For example, during the data collection cycle, contrast agents are destroyed by substantially full power acoustic waveforms associated with color Doppler imaging. During other portions of the cardiac cycle, contrast agents are allowed to enter the imaged region of the subject and are not destroyed by the reduced power waveforms associated with B-mode imaging.

Figure 3A:
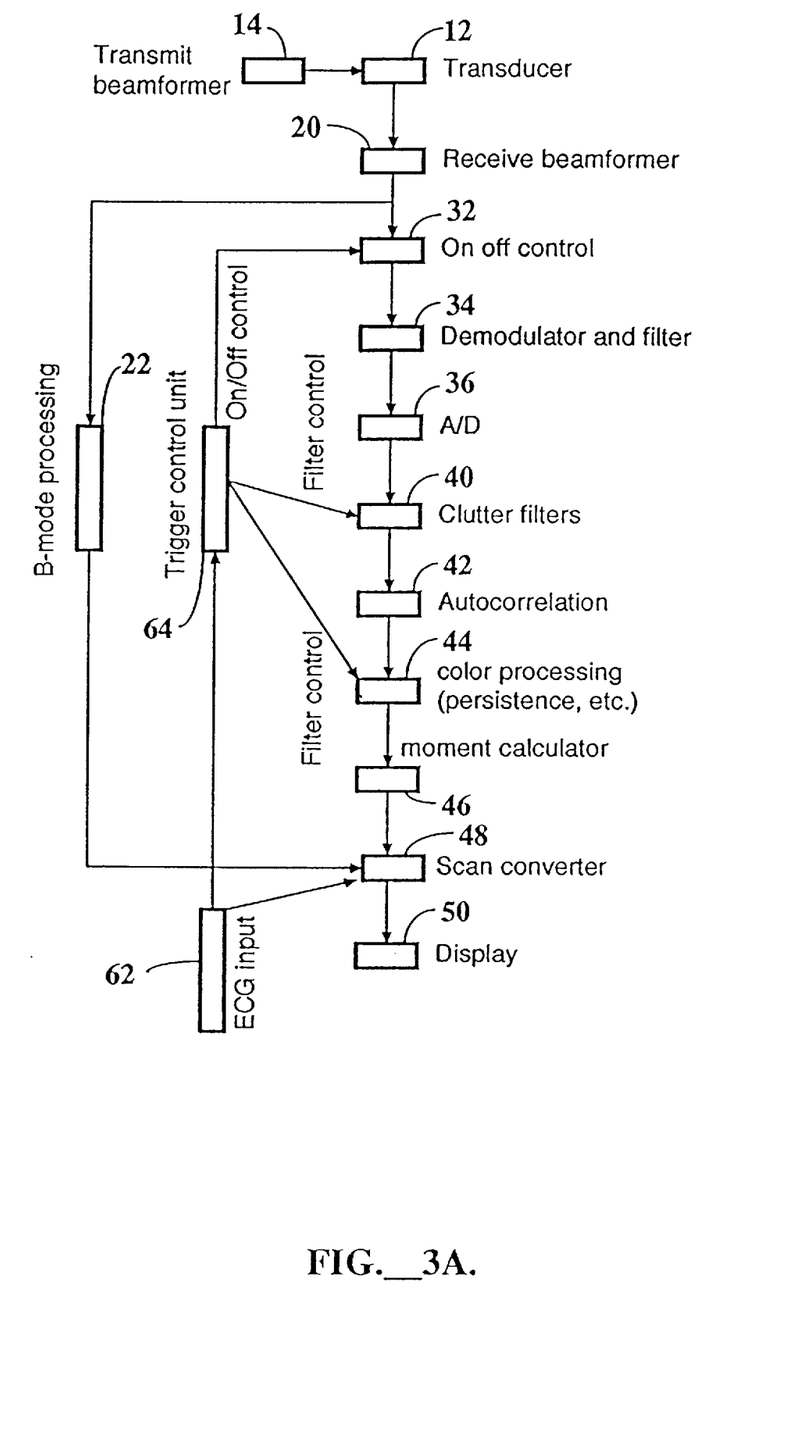
FIG. 3A is a block diagram of an ultrasound imaging system for imaging tissue and blood flow to illustrate a second embodiment of the invention.
Figure 3B:
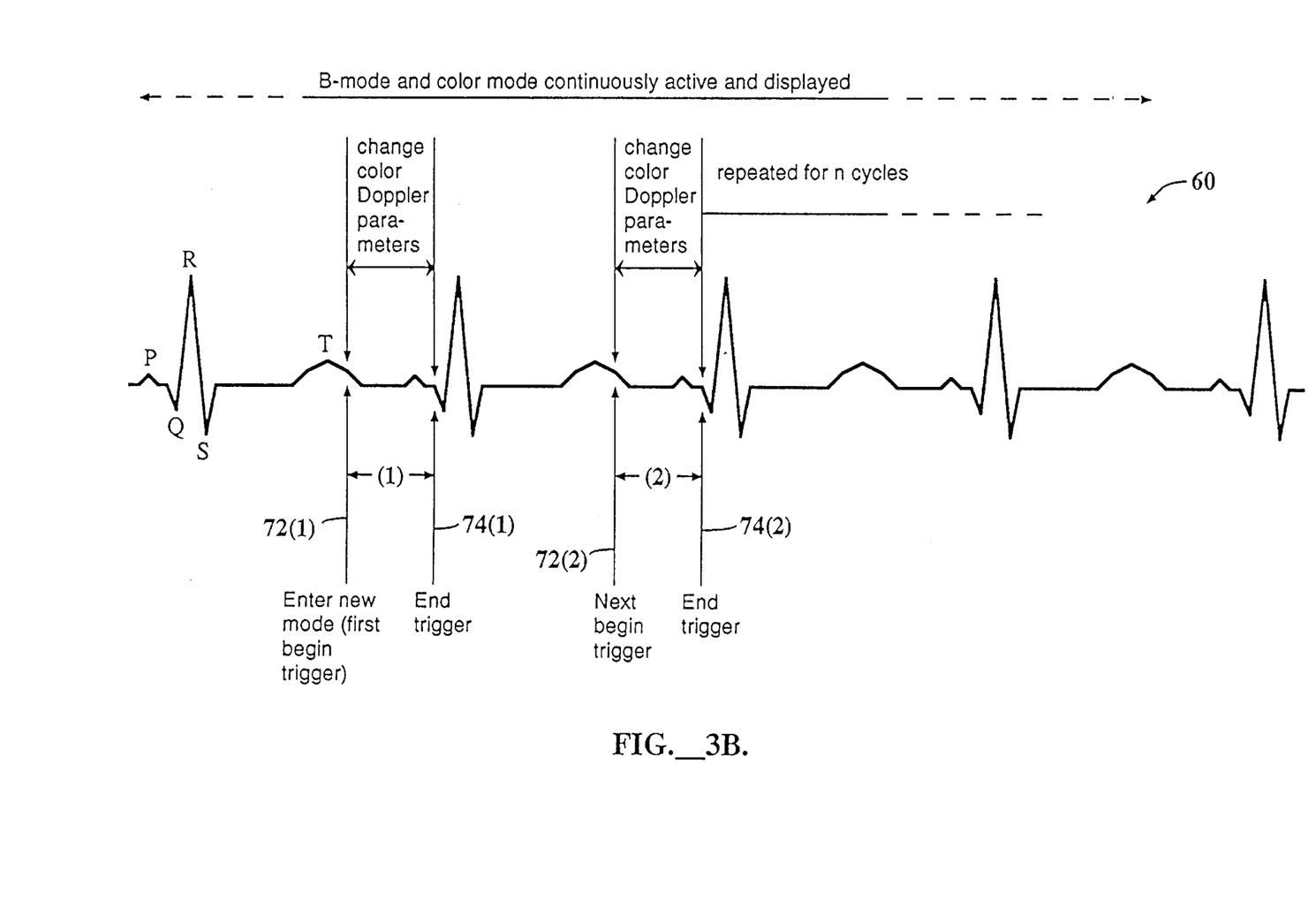
FIG. 3B is a graphical illustration of the EKG waveform for illustrating the operation of the system of FIG. 3A.

In order to improve sensitivity of the system for detecting myocardial perfusion, it may be desirable to change the system parameters, such as by essentially reducing the filtering action by clutter filters 40 of the Doppler signal. This is illustrated in FIGS. 3A, 3B. In reference to FIGS. 2A, 3A, system 100 of FIG. 3A differs from system 10 of FIG. 2A only in that the trigger control unit 64 also provides control signals to clutter filters 40; these signal paths are not present in system 10 of FIG. 2A. In reference to FIG. 3B, both B-mode and color acquisition are always active and only the system parameters in the color processing signal path respond to the triggers. The B-mode and color data is associated with fundamental or harmonic frequency bands as discussed above. As in the case of system 10, the user through a suitable user interface may select a particular point or points in the cardiac cycle (or any portion of the cycle less than a complete cycle) in order to generate trigger signals for triggering the change in system parameters in system 100. At time 72(1), for example, a begin trigger may be generated by unit 64 to change the filter coefficients applied by clutter filters 40 and the spatial and/or temporal filters in color processing unit 44 to enhance sensitivity and accuracy of detection. In the time period between times 72(1) and 74(1) the heart walls are essentially stationary. Hence, heart wall movement will be at a minimum and the coronary artery flow is at its maximum. For this reason, the filter coefficients of clutter filters 40 may be altered to remove or reduce the effect of the filters 40 in order to enhance sensitivity of detection. At time 74(1), the filter coefficients of filters 40 may be restored to apply effective clutter filtering to the color Doppler signals.

The trigger control unit 64 also provides control signals to the color processing unit 44 to alter the coefficients of the temporal filters in unit 44 in order to temporally persist information at end-diastole at time 74(1). This will improve myocardial border estimations in blood pool measurements and prevent the color Doppler velocity signal from falling to zero.

More than one set of begin and end triggers may be employed to independently control multiple functions and multiple parameters. For instance, one set of triggers could be set along the EKG waveform at the beginning of diastole to change temporal persistence parameters and the end trigger positioned at end diastole to terminate persistence behavior as described above. Another set of triggers positioned along the same EKG waveform would control a different set of behaviors during systole. The systole trigger could be used to modify a new or different level of persistence behavior optimized for the systole time frame.

A signal path is also provided between unit 64 and on/off control switch 32 in system 100, so that unit 64 may generate begin as well as end-triggers for controlling the time period during which a color Doppler mode is initiated, by enabling or disabling the Doppler signal path. Such and other variations are within the scope of the invention.

Triggers may also be used to change parameters associated with fundamental or harmonic band data. For example, the color Doppler data switches between data associated with harmonic and data associated with fundamental frequencies. The switching is done in response to triggers. Triggers may also be used to change parameters associated with imaging contrast agents. For example, the color Doppler data switches between data associated with substantially full power and data associated with reduced power waveforms. The switching is done in response to triggers. Preferably, the B-mode data not responsive to the triggers is associated with reduced power waveforms to avoid destruction of the contrast agents. Various other combinations of type of data and triggers may be provided, such as harmonic based B-mode data responsive triggers and fundamental based color-Doppler data not responsive to triggers.

Figure 4A:
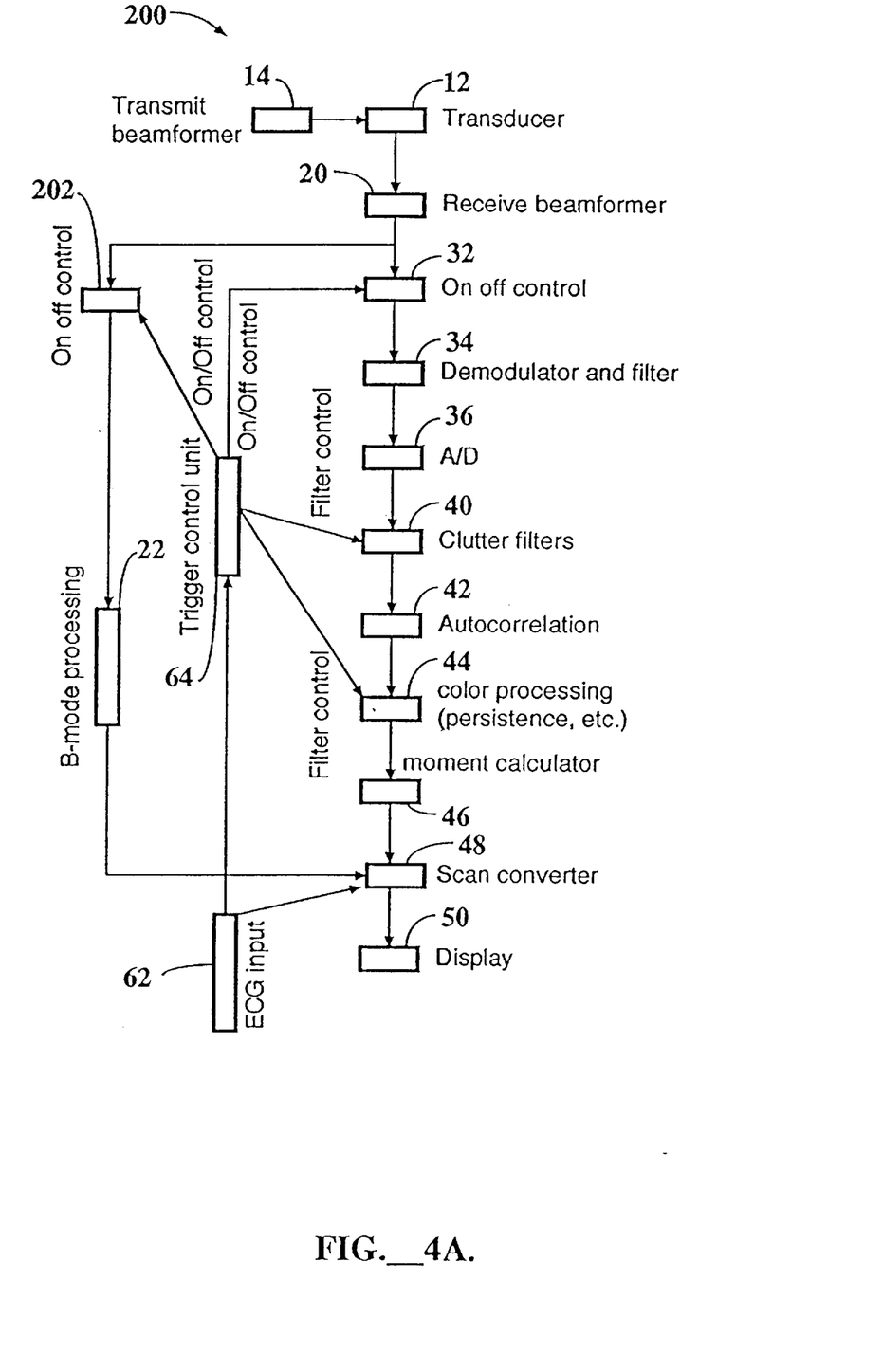
FIG. 4A is a block diagram of an ultrasound imaging system for imaging tissue and blood flow to illustrate a third embodiment of the invention.

FIG. 4A is a block diagram of an ultrasound imaging system 200 to illustrate a third embodiment of the invention. System 200 differs from system 100 of FIG. 3A in that an on off control unit 202 is employed in the B-mode data path and a control signal path is provided between control unit 64 and unit 202 so that B-mode data acquisition and display may be controlled as a function of particular trigger times or time periods selected by the user. In addition, in the control path between unit 64 and color processing unit 44, control unit 64 is capable of controlling the processing unit 44 so that unit 44 monitors and compares the incoming Doppler data sample to the stored prior sample. If a subsequent sample value (such as mean velocity, energy, variance or a parameter that is a function of any one or more of the three quantities) is of a greater amplitude than a previously acquired sample value at a spatial location, it is used to replace the previous sample value to be displayed. But if the subsequent sample value is not of a greater amplitude than a previously acquired sample value, then the previously acquired sample value is retained instead for display. In this manner the highest sample value is accumulated in a sequence of accumulated frames and the display 50 displays the accumulated frames. This enhances the detection of weak motion in the body imaged. The different modes of operation of system 200 are illustrated below in reference to FIGS. 4B–4D.

In any of the various modes of operation, data associated with harmonic or fundamental frequency bands may be used as discussed above. Likewise, contrast agents may or may not be used.

Figure 4B:
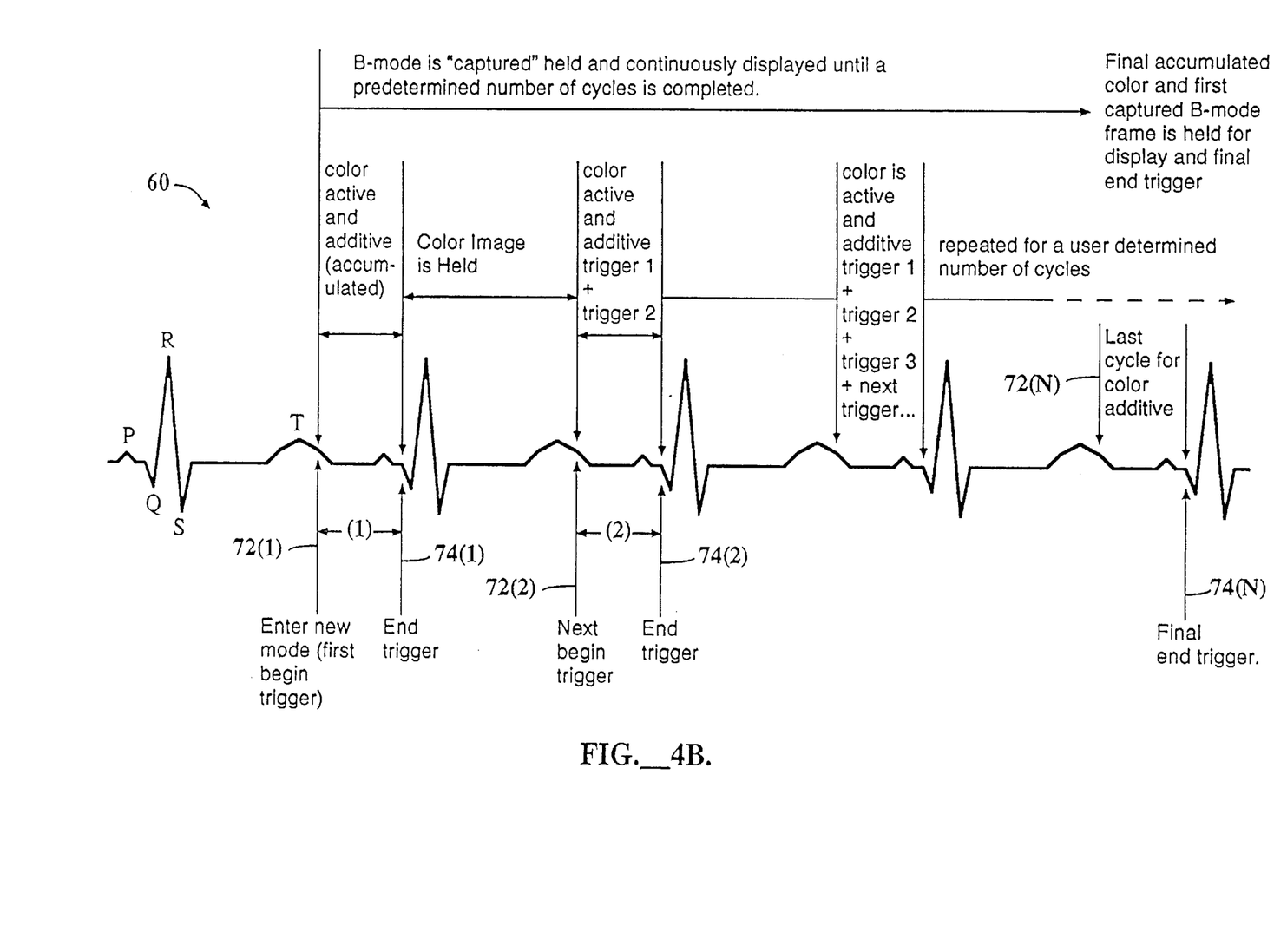
FIGS. 4B, 4C, and 4D are graphical illustrations of EKG waveforms to illustrate different modes of operation of the system of FIG. 4A.

FIG. 4B is a graphical illustration of EKG waveform 60 to illustrate one mode of operation of system 200 of FIG. 4A. Trigger control unit 64 supplies a first begin trigger 72(1) to switch 32 so as to enable the acquisition of color Doppler data. At the same time, unit 64 also sends a begin trigger to on/off control unit 202 to enable the acquisition of a B-mode frame after which the B-mode data path is automatically turned off by control unit 202. B-mode processing unit 22 supplies such captured B-mode frame to scan converter 48 so that such frame is displayed continuously until a predetermined number of cycles have been completed. Control unit 64 may also be used to supply control signals to control the coefficients of clutter filters 40 and the spatial and temporal filters in unit 44 in the manner described above in reference to FIGS. 3A, 3B.

In addition, control unit 64 may also be used to send a control signal to unit 44 in order to combine at least some of the multiple frames of color Doppler data to obtain a sequence of accumulated frames in the manner described above. Thus, if a sample value (such as mean velocity, energy, variance or a parameter that is a function of any one or more of the three quantities) at a spatial location in the subsequent incoming frame is of a greater amplitude than the sample value of a previously acquired frame, it is used to replace the sample value of a previously acquired frame to be displayed. But if the sample value of the subsequent incoming frame is not of a greater amplitude than a previously acquired sample value, then the sample value of the previously acquired frame is substituted for the sample value of the incoming frame for display. This process is repeated for all locations of the frame and the resulting frame is called an "accumulated frame." Hence, each accumulated frame contains pixel values that are the up-to-date highest values at each spatial location. This process is referred to in this application as "additive," and the frames that result from such operation is referred to as accumulated frames. Such process defines a combining step for the incoming frame and the previously acquired frame. In the preferred embodiment, such combining step is performed for at least some of the multiple frames of the color Doppler data to obtain accumulated frames with the highest pixel values of the multiple frames. From the operation, a sequence of accumulated color Doppler data frames is obtained.

As also shown in FIG. 4B, throughout the N data collection cycles, color Doppler data acquisition is performed and the acquisition of color Doppler data is additive. Between the end trigger of one data collection cycle and the begin trigger of the next data collection cycle, the last color Doppler data frame acquired during the last data collection cycle displayed on the display 50 is continuously displayed and held unchanged. As also shown in FIG. 4B, the color Doppler data acquired is additive over the N data collection cycles until the final end trigger 74(N) is reached. In other words, at the begin trigger 72 (2), color processing unit 44 still stores the last color Doppler frame that was acquired during the data collection cycle (1). After the first frame of the data collection cycle (2) has been acquired in response to the begin trigger at time 72 (2), unit 44 then compares the pixel values of such frame to the pixel values of the frame stored to obtain an additively accumulated frame in the manner described above.

This process is also performed at the beginning of each of the subsequent data collection cycles so that the color Doppler data is additive over all N-cycles in FIG. 4B, and only the highest pixel values that occur at any point during the N-data collection cycles are displayed. This is particularly advantageous for detecting weak signals such as myocardial perfusion. This increases the concentration of color Doppler signal available for display and is important for collection and reinforcement of color data of blood flow over poorly perfused tissue segments within the heart.

Figure 4C:
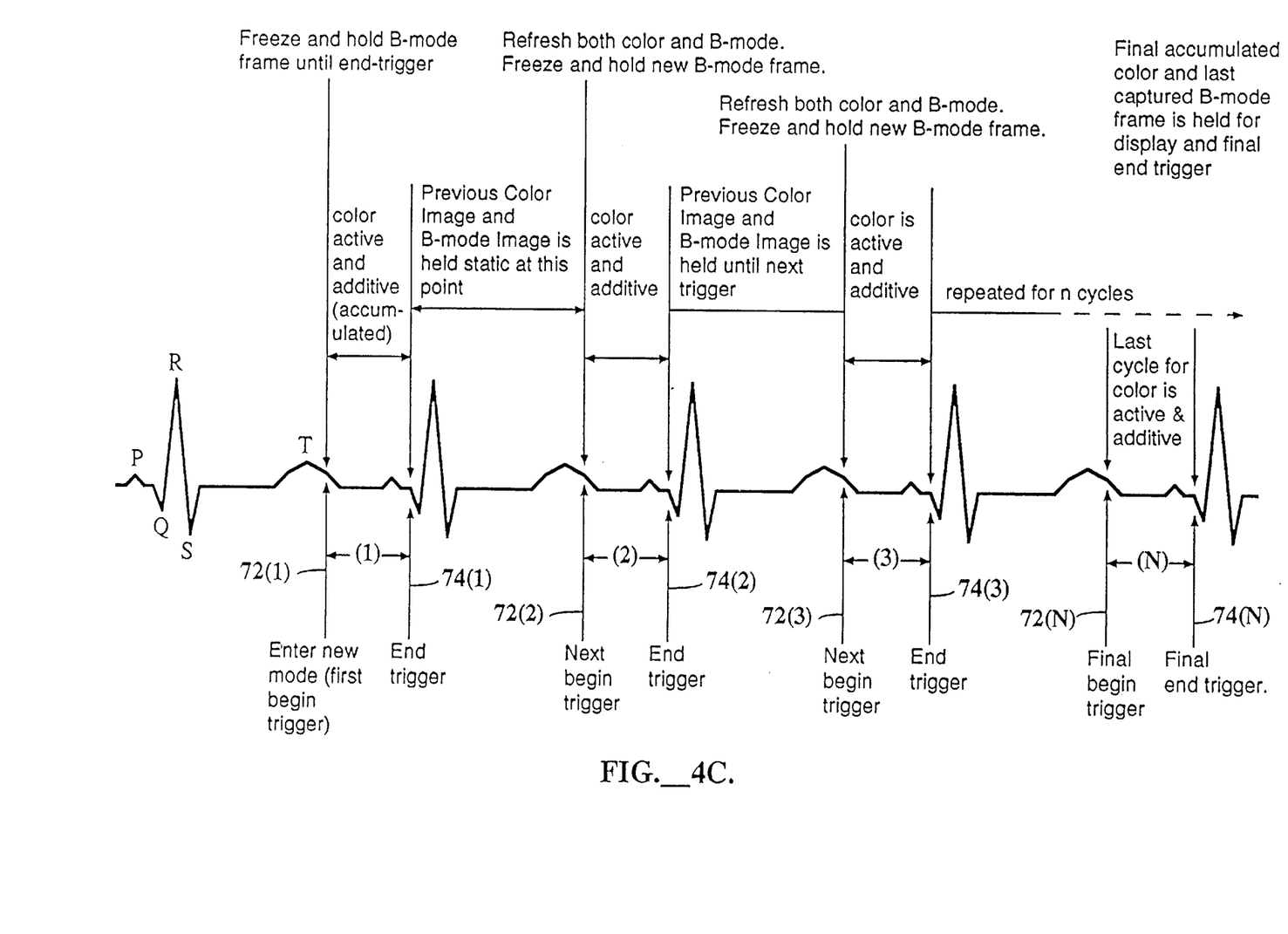

The embodiment of FIG. 4B is particularly useful when the patient is able to hold his breath and lay motionless for a prolonged duration over several cardiac cycles. This is the case since the B-mode image first acquired is held and continuously displayed over several cardiac cycles. The embodiment of FIG. 4C differs from that of FIG. 4B in that the color Doppler data is additive only during a single data collection cycle and that both the color Doppler data and the B-mode data in the frame are refreshed upon the begin trigger of each of the N-data collection cycles. The embodiment of FIG. 4C is advantageous for patients who cannot rest comfortably or quietly, such as uncooperative patients or small children. Extraneous motion is less of a problem because the data is refreshed with each new begin trigger of a new data collection cycle. Thus, upon the begin trigger at time 72 (2), the previously stored color Doppler data as well as B-mode data in the last frame of the prior data collection cycle are replaced by that acquired in response to the begin trigger of the second data collection cycle (2). As in the embodiment of FIG. 4B, during the interim time periods between data collection cycles, the last frame (both B-mode and color Doppler data) of the prior data collection cycle is held static and displayed by display 50 until the time of the begin trigger of the next data collection cycle.

Figure 4D:
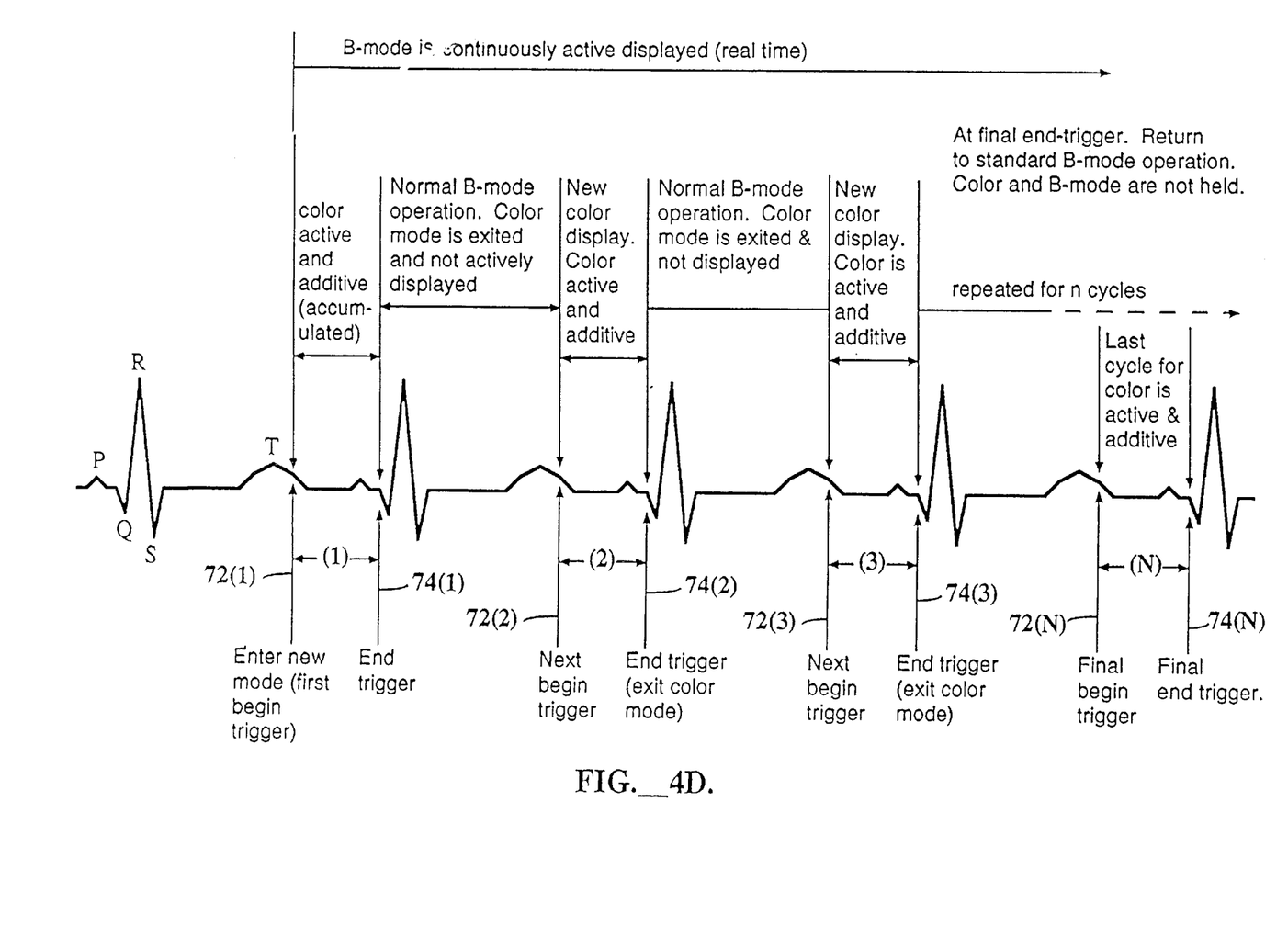

The embodiment of FIG. 4D differs from that of FIG. 4C only in that instead of refreshing the B-mode frame only upon receiving the begin trigger of each data collection cycle, the B-mode is continuously active and displayed in real time.

SUMMARY OF CHARACTERISTICS OF THE OPERATION MODES IN FIGS. 2B, 3B, 4B–4D

I. FIG. 2B
1. Image tissue and fluid
   A. B-mode behavior—B-mode is active and continuous (real time) throughout the cardiac cycle regardless of triggers.
2. Begin-trigger
   A. Enters color Doppler mode and is active and displayed until the end-trigger point is reached 3. End-trigger
   A. Exits color Doppler mode and no color Doppler is displayed until next begin trigger
4. Final and Exit Trigger
   A. Begin-End sequence is repeated for n cycles until the trigger is exited By turning on and off color Doppler in this manner, the user is able to look on at the myocardial tissue blood flow at a specific segment in the cardiac cycle. This will eliminate most extraneous color Doppler noise created by myocardial tissues and chamber blood flow. (Note: in this mode the color Doppler is only turned on and off during the cardiac cycle.)

II. FIG. 3B
1. Image tissue and fluid
   A. B-mode behavior—B-mode is active and continuous (real time) throughout the cardiac cycle regardless of triggers
   B. Color behavior—color Doppler is active and continuous (real time) throughout the cardiac cycle but in addition, modifies selected parameters from trigger begin and end points
2. Begin-trigger
   A. Enter selected color Doppler mode
   B. Modify one or more color Doppler parameters including but not limited to:
      a. persistence
      b. Doppler baseline
      c. pre-processing
      d. post-processing
      e. gate or filters
      f. other Doppler parameters
      g. fundamental or harmonic demodulation
      h. power level of associated acoustic waveforms
3. End-trigger
   A. At end-trigger return to pre-trigger state.
4. Final and Exit trigger
   A. Being-End sequence is repeated for n cycles until the trigger is exited by user In this situation, both the B-mode and color Doppler are allowed to remain on continuously throughout the entire cardiac cycle. In this configuration, certain selectable color Doppler parameters are modified for specific segments of the cardiac cycle. This provides a greater control of color parameters than previously possible. This gives the user the ability to match the temporal qualities of the heart with the temporal characteristics of the imaging device.

This will be useful in examining blood pools (cardiac chambers), coronary artery flows, and tissue (myocardial) blood flows.

The Doppler baseline can be changed in response to the direction of the blood flow, allowing an increase in the color alias limits imposed by having the baseline in the center of the color map. (With baseline position switching from top to bottom of scale, the Doppler's effective Nyquist limit has been increased.)

III. FIG. 4B
1. Image tissue and fluid
   A. B-mode behavior
      a. Acquire 1 B-mode frame at begin-trigger and hold displayed image on video screen at begin trigger
      b. Hold captured video frame across all subsequent trigger begin and end points
   B. Color Doppler mode behavior
      a. At begin-trigger, activate color Doppler and accumulate color Doppler information- while the trigger is active
      b. At end-trigger, color Doppler mode is held static at point of exit trigger along with the B-mode information
   C. Next trigger cycle
      a. At next begin-trigger, reactivate color Doppler mode and add newly acquired color Doppler information to previously captured and held B-mode and color Doppler frame
   D. Exit trigger cycle
      a. Trigger is exited after a predetermined number of cycles as selected by the user
      b. Final acquired image is held and displayed as a static video frame This allows an accumulation of color Doppler signals over time, thereby increasing the concentration of color Doppler signal available for display over tissue. This is important for collection and reinforcement of color data over poorly perfused tissue segments within the heart.

This is useful when the patient is able to hold his breath and lay motionless for a prolonged duration over several cardiac cycles.

IV. FIG. 4C
1. Image tissue and fluid
   A. B-mode behavior
      a. Begin-trigger B-mode frame is frozen and held static on the video display until next begin-trigger (at which time the B-mode is refreshed and new B-mode image is acquired)
   B. Color Doppler mode behavior
      a. At begin-trigger, activate color Doppler and accumulate color Doppler information while trigger is active (until end-trigger)
      b. At end-trigger, both color Doppler and the acquired B-mode are held static until the next begin-trigger
      c. Next begin-trigger, acquire new B-mode (refresh B-mode) and acquire new color Doppler (refresh color Doppler)
   C. Exit trigger cycle
      a. Trigger is exited after a predetermined number of cycles as selected by the user or n cycles until user manually exits the mode
      b. Final acquired image is held and displayed as a static video frame This also allows an accumulation of color Doppler signals over time and increases the concentration of color Doppler signal available for display over tissue. However, the advantage here is that the B-mode and color Doppler are refreshed with each new begin trigger. This reduces the effect that motion translation artifact has on subsequent images.

This is useful in a patient that cannot rest comfortably or quietly; uncooperative patients or small children. Extraneous motion is less of a problem for this configuration because the data is refreshed with new begin-triggers.

V. FIG. 4D
1. Image tissue and fluid
   A. B-mode behavior (continuous real-time B-mode)
      a. B-mode is active and continuously displayed regardless of begin and end-trigger points.
   B. Begin-trigger
      a. Activate, accumulate and display color Doppler until end-trigger
   C. End-trigger
      a. Exit color Doppler mode and do not display or hold accumulated color Doppler information on the video display D. Next begin-trigger
   a. Repeat previously described begin-trigger and end-trigger behavior (step B.a. and step C.a.)
E. Exit trigger cycle
   a. Trigger is exited after a predetermined number of cycles as selected by the user or n cycles until user manually exits the mode In this case, the B-mode is always active and in real-time. This allows for the greatest amount of patient motion with lesser artifacts. This is useful for the myocardial tissue blood flow and coronary artery flow.

In General

Out of all the configurations, those of FIGS. 3B and 4D are particularly preferred: that of FIG. 3B in regard to control of imaging parameters and that of FIG. 4D in its ability to gather tissue blood flow information for a given cardiac segment. The continuous B-mode acquisition in the case of FIG. 4D will be the most intuitive for clinical customers.

While in the embodiments described above, each data collection cycle occurs at the same position of the cardiac cycle, (that is, at constant relative timing relationship to a particular point in the cardiac cycles, such as the R-wave), it will be understood that this is not required. If desired, such data collection cycles may occur over different portions of the cardiac cycles and two or more data collection cycles can occur within the same cardiac cycle. Such and other variations are within the scope of the invention. Furthermore, multiple trigger signals at any number of user selectable points of the cardiac cycle may be employed to change color Doppler or B-mode imaging parameters. This would be most important in the FIGS. 2B and 3B imaging protocols described above.

While begin and end triggers are used to control the color Doppler data acquisition as well as, in some cases, the B-mode data acquisition in the embodiments described above, it will be understood that other methods for control and for specifying data collection cycles may be used and are within the scope of the invention. For example, a begin trigger may be used to initiate color Doppler data acquisition in the same manner as described above, but such acquisition may be ended at a predetermined time after the begin trigger, instead of at a time when an end trigger is received as described above. Such predetermined time period may be the same or different for the N data collection cycles.

Instead of using the EKG waveform for deriving a trigger, other signals indicative of a cardiac cycle may be used for this purpose, such as signals derived from phonocardiogram, pressure wave, pulse wave or respiratory signal waveforms. Other waveforms that can be used to produce a trigger include a pulse wave or continuous wave Doppler, m-mode strip display, and all physio recording devices including; pulse pressure wave forms, heartsound waveforms, and respiratory waveforms. The advantage of any such triggers over, for example, triggers determined by user input is that such triggers avoid the variability that would be associated with user-determined triggers of points in a cardiac cycle.

In the preferred embodiment described above, at least some of the multiple frames of the color Doppler data are compared to obtain accumulated frames with the highest pixel values of the multiple frames. Such operation is referred to above as "additive" and the frames that result from such operation is referred to as an accumulated frame. It will be understood, however, that the multiple frames of the color Doppler data may be combined in other ways to optimize the data acquisition and display and to obtain accumulated frames. Such and other variations are within the scope of the invention.

While the invention has been described above by reference to various embodiments, it will be understood that different changes and modifications may be made without departing from the scope of the invention which is defined only by the appended claims and their equivalents.

What is claimed is:

1. A method for ultrasonic imaging, the method comprising the steps of:
   a) generating begin and end triggers in response to waveform information;
   b) acquiring in response to the begin trigger a plurality of frames of imaging data, each of the plurality of frames associated with a harmonic frequency band; and
   c) ending the acquisition of step (b) in response to the end trigger.

2. The method of claim 1 wherein the step (b) comprises the step of acquiring imaging data associated with a second harmonic frequency band.

3. The method of claim 1 wherein the step (b) comprises the step of acquiring color Doppler data selected from the group of: color Doppler velocity, color Doppler energy, color Doppler variance and combinations thereof.

4. The method of claim 1 wherein the step (b) comprises the step of acquiring B-mode data.

5. The method of claim 1 further comprising the step (d) of substantially continuously acquiring B-mode data during a waveform cycle; and wherein the step (a) comprises generating the begin and end triggers during the waveform cycle.

6. The method of claim 5 wherein the step (d) comprises acquiring B-mode data associated with harmonic frequencies.

7. The method of claim 5 further comprising the step (e) of providing contrast agents within an imaged subject and wherein the steps (b) and (d) comprise avoiding destruction of the contrast agents from the transmission of the acoustic waveforms.

8. The method of claim 1 wherein the step (a) comprises generating a plurality of begin and end triggers in response to a respective plurality of cycles of the waveform information; and wherein the step (b) comprises acquiring the plurality of frames of imaging data in response to each of the plurality of begin triggers.

9. The method of claim 8 wherein the step (c) comprises ending the acquisition of imaging data after each of the plurality of end triggers.

10. The method of claim 1 further comprising the step (d) of providing contrast agents within an imaged subject.

11. The method of claim 10 wherein the step (b) comprises transmitting acoustic waveforms associated with reduced power.

12. The method of claim 11 wherein the step (b) comprises avoiding destruction of the contrast agents from the transmission of the acoustic waveforms.

13. The method of claim 1 further comprising:
   the step (d) of acquiring other imaging data before the begin trigger, the other imaging data associated with a substantially same mode as the imaging data; and
   the step (e) of changing in response to the begin trigger at least one parameter associated with the other imaging data for acquiring the imaging data.

14. The method of claim 13 wherein the step (c) comprises changing the at least one parameter in response to the begin trigger.

15. The method of claim 14 further comprising the step (d) of repeating the steps (a), (b) and (c) for a plurality of cycles of the waveform information.

16. The method of claim 14 wherein the step (c) comprises changing a frequency band associated with the imaging data from the harmonic frequencies to fundamental frequencies.

17. The method of claim 14 further comprising the step (d) of providing contrast agents.

18. The method of claim 17 wherein the step (c) comprises changing a power level of acoustic waveforms.

19. The method of claim 13 wherein the steps (b) and (c) comprise acquiring color Doppler mode data.

20. The method of claim 1 wherein the step (a) comprises generating the begin and end triggers in response to EKG information.

21. A method for ultrasonic imaging, the method comprising the steps of:
   a) providing at least one begin and end signals in response to EKG information, the at least one begin and end signals associated with first and second points, respectively, in a cardiac cycle;
   b) acquiring at least one frame of B-mode information during the cardiac cycle; and
   c) acquiring between the begin and end signals a plurality of frames of imaging information associated with harmonic frequencies, the imaging information selected from the group of: B-mode information and color Doppler information.

22. The method of claim 21:
   further comprising the step (d) of providing contrast agents; and
   wherein the step (b) comprises the step of transmitting acoustic waveforms associated with power levels reduced from a maximum power level.

23. An apparatus for ultrasonic imaging, the apparatus comprising:
   a) a waveform input;
   b) means for generating begin and end triggers in response to information from the waveform input;
   c) a data path for acquiring in response to the begin trigger a first plurality of frames of imaging data, each of the first plurality of frames associated with a harmonic frequency band, and for ending the acquisition in response to the end trigger.

24. The apparatus of claim 23 further comprising:
   a) a means for acquiring before the begin trigger a prior plurality of frames of imaging data, the prior plurality of frames of imaging data corresponding to a substantially same mode as the first plurality of frames of imaging data; and
   b) a means for changing in response to the begin trigger at least one parameter associated with the prior plurality of frames for acquiring the first plurality of frames of imaging data.

* * * * *